United States Patent [19]

Saito et al.

[11] 4,430,500
[45] Feb. 7, 1984

[54] PROCESS FOR PURIFYING CEPHALOSPORIN COMPOUNDS

[75] Inventors: Hideomi Saito, Sagamihara; Tomoya Yamamoto; Masayuki Nomura, both of Yokohama; Tomoyoshi Hachiya, Kunitachi, all of Japan

[73] Assignee: Ajinomoto Co., Inc., Tokyo, Japan

[21] Appl. No.: 388,656

[22] Filed: Jun. 15, 1982

[30] Foreign Application Priority Data

Jun. 16, 1981 [JP] Japan ................................. 56-92837

[51] Int. Cl.$^3$ ........................................... C07D 501/04
[52] U.S. Cl. ..................................... 544/25; 424/246
[58] Field of Search ........................... 544/25; 424/246

[56] References Cited

U.S. PATENT DOCUMENTS 4,217,450 8/1980 Yasuda et al. ...................... 544/25

Primary Examiner—Nicholas S. Rizzo
Attorney, Agent, or Firm—Oblon, Fisher, Spivak, McClelland & Maier

[57] ABSTRACT

A cephalosporin compound of the formula:

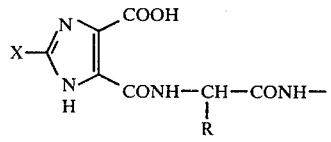
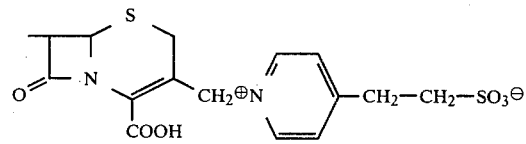

wherein X is hydrogen, halogen, hydroxy, alkyloxy, aralkyloxy, aryloxy, mercapto, alkylthio, aralkylthio, arylthio, alkylsulfonyl, aralkylsulfonyl, arylsulfonyl, alkylsulfinyl, aralkylsulfinyl, arylsulfinyl, amino, mono- or di-alkylamino, mono- or di-aralkylamino, mono- or di-arylamino, acylamino, a sulfonic acid group, nitro, alkyl, aralkyl, aryl or a heterocyclic group; R is hydrogen, alkyl, aralkyl, aryl or a heterocyclic group, with all of the alkyl, aralkyl, aryl and heterocyclic ring groups in radicals X and R optionally being substituted with at least one substituent, is purified by (a) adjusting the pH of an aqueous solution containing said cephalosporin compound to be purified to within the range of 1.0 to 3.5; (b) isolating the compound which precipitates from said solution; (c) after concentration adding the resulting mother liquor to the organic solvent, isolating the precipitated compound and agitating the obtained compound in an aqueous solution in the presence of an absorbing resin which is a hydrophilic, high molecular weight material having a fine network structure; and (d) isolating the purified compound.

9 Claims, No Drawings

PROCESS FOR PURIFYING CEPHALOSPORIN COMPOUNDS

BACKGROUND OF THE INVENTION

The present invention relates to a process for purifying cephalosporin compounds.

SUMMARY OF THE INVENTION

One object of the present invention is to provide cephalosporin compounds of enhanced purity for the treatment of subjects having an infectious disease.

Briefly, this object and other objects of the present invention as hereinafter will become more readily apparent can be attained by a process for purifying a cephalosporin compound of the formula:

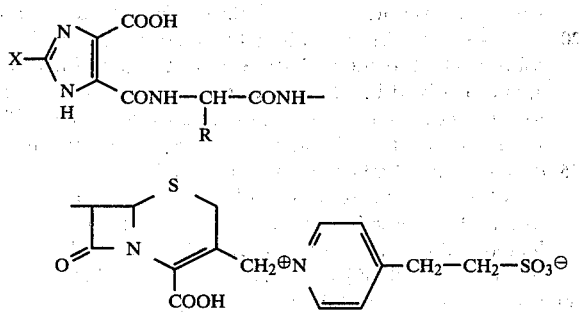

wherein X is hydrogen, halogen, hydroxy, alkyloxy, aralkyloxy, aryloxy, mercapto, alkylthio, aralkylthio, arylthio, alkylsulfonyl, aralkylsulfonyl, arylsulfonyl, alkylsulfinyl, aralkylsulfinyl, arylsulfinyl, amino, mono- or di-alkylamino, mono- or di-aralkylamino, mono- or di-arylamino, acylamino, a sulfonic acid group, nitro, alkyl, aralkyl, aryl or a heterocyclic group; and R is hydrogen, alkyl, aralkyl, aryl or a heterocyclic group, with all of the alkyl, aralkyl, aryl and heterocyclic ring groups in radicals X and R optionally being substituted with at least one substituent, comprising (a) adjusting the pH of an aqueous solution containing said cephalosporin compound to be purified to within the range of 1.0 to 3.5; (b) removing the compound which precipitates from said solution; and (c) after concentration adding the resulting mother liquor to the organic solvent, isolating the precipitated compound and agitating the obtained compound in an aqueous solution in the presence of an absorbing resin which is a hydrophilic, high molecular weight material having a fine network structure; and (d) isolating the purified compound.

DETAILED DESCRIPTION OF THE PREFERRED EMBODIMENTS

The present invention relates to a process for purifying cephalosporin compounds which are effective as antibacterial agents, particularly as medicinal compounds for treating infectious diseases of human beings and animals caused by *Pseudomonas aeruginosa*, or as intermediates for the preparation of other medicinal agents. They key feature of the present invention is the removal of impurities from the cephalosporin compound (see U.S. Pat. No. 4,217,45) by treatment of the compound with an absorbing resin. The present cephalosporin compound is a compound of the formula:

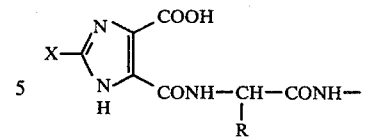
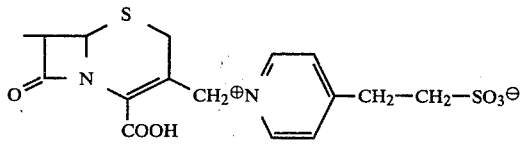

as described in Japanese Patent Application (OPI) No. 76887/80. In the formula, radical X represents a hydrogen atom, an alkyl-, aralkyl- or aryloxy group, a mercapto group, an alkyl-, aralkyl- or arylthio group, an alkyl-, aralkyl- or arylsulfonyl or -sulfinyl group, an amino group, a mono- or di-alkyl-, aralkyl- or arylamino group, an acylamino group, a sulfonic acid group or a nitro group, or a radical such as an alkyl group, an aralkyl group, an aryl group or a hetero ring group, and R represents a hydrogen atom or an alkyl group, an aralkyl group, an aryl group, or a hetero ring group. Additionally, all of the alkyl groups, aralkyl groups, aryl groups, and hetero ring groups which make-up many of the different radicals of groups X and R optionally may have one or more substituents.

The present cephalosporin compound can be prepared by any one of a number of different synthesis procedures such as, for example, by reacting a compound of the formula:

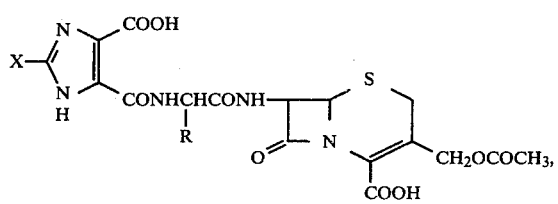

wherein X and R are the same as defined above with 4-pyridineethanesulfonic acid in an aqueous solution in the presence of sodium iodide. However, the crude product obtained from the synthesis technique, no matter which method is used, is contaminated with colored impurities produced by competing side reactions. These impurities have been very difficult to remove even by purification methods such as reprecipitation or recrystallization. For example, in the above-described specific reaction, after the reaction is conducted in the presence of sodium iodide, an organic solvent, which dissolves sodium iodide but which does not dissolve the end product, such as methanol, ethanol, propanol, acetone or methyl ethyl ketone is added to the reaction solution (from which solids are removed if any are present) to separate the end product as a solid product. Alternatively, an aqueous solution containing the end product may be added to the above-described organic solvent. The end product can be obtained by repeating this procedure several times. However, the product obtained is still unsatisfactory from the viewpoint of a safe product which exhibits no biological toxicity. Because of this problem, there has been a continuing need for the development of a process for the purification of cephalosporin compounds to a high state of purity in high yield.

It has now been found that purified cephalosporin compounds of the indicated structure can be obtained by contacting an impure cephalosporin compound in solution with a hydrophilic, high molecular weight resin. A preferred embodiment of the present process is as follows.

A reaction solution containing the desired product is added to a 3- to 7-fold volume of an organic solvent such as methanol, ethanol, propanol, acetone or methyl ethyl ketone cooled to 5° to 20° C., and the precipitate which forms is removed by filtration or centrifugation. In reactions which use sodium iodide, sodium iodide can be removed in the mother liquor. The thus obtained precipitate is dissolved in water, and again a 3- to 7-fold volume of the aforesaid organic solvent is added to the product and a precipitate is formed. The precipitate is separated thereby yielding an impure, crude product. Repetition of this procedure yields a crude product of higher purity.

This crude product is dissolved in water and, after adjusting the concentrations of 1–10%, preferably 2–4%, an inorganic acid such as hydrochloric acid, sulfuric acid or nitric acid or an organic acid such as formic acid, acetic acid or oxalic acid is added thereto to adjust the pH of the solution to 1.0 to 3.5, preferably 1.5 to 2.5, in order to precipitate impurities. The temperature of the solution during this procedure is suitably 10° to 35° C., preferably 25° to 30° C. The precipitate which forms is removed by filtration or centrifugation, and the resulting mother liquor is concentrated to 10–15% at 20° to 40° C., preferably 20° to 30° C., and is added to a 3- to 7-fold volume of the organic solvent as described above at a low temperature of 5° to 20° C. to precipitate the end product. The precipitated product is separated by filtration or centrifugation. Water is added to the thus separated precipitate thereby making a 5–20% by weight aqueous solution, and is preferably adjusted to a pH of 3 to 4 in view of the good recovery of the desired product compound achieved and the excellent extent to which impurities are removed. The impurities present in the compound are removed by contact with a 0.1 to a ten-fold volume of a hydrophilic, high molecular weight resin having a fine network structure such as "Amberlite XAD-7, XAD-8" made by Rohm & Haas Co. or "Diaion HP-1MG, HP-2MG or HP-3MG" made by Mitsubishi Chemical Industries, Ltd. The contact can occur as a batch process or as a chromatographic purification process.

The thus obtained aqueous solution containing the end product is concentrated to a concentration of 10 to 15% at a low temperature of 20° to 30° C., and a 3- to 7-fold volume of an organic solvent as described above cooled to 5° to 20° C. is added thereto to precipitate the end product. After being separated by filtration or centrifugation, the precipitate is dried in a conventional manner to obtain the highly purified end product. The thus purified cephalosporin compounds are stable products which exhibit absolutely no biochemical toxicity.

Having generally described this invention, a further understanding can be obtained by reference to certain specific examples which are provided herein for purposes of illustration only and are not intended to be limiting unless otherwise specified.

EXAMPLE 1

A 7.13 g (13.1 mmol) amount of 7 β-[D-(−)-α-(4-carboxyimidazole-5-carboxamido)-phenylacetamido]-cephalosporanic acid and 4.9 g (26.3 mmol) of 4-pyridineethanesulfonic acid were suspended in 30 ml of water, and the pH of the solution was adjusted to 6.5 with 2 N sodium hydroxide to dissolve the reactants. After adding thereto 87.5 g of sodium iodide, the stirred mixture was heated to 65° C. for 70 minutes to complete the reaction. After being cooled, the reaction solution was dropwise added to 330 ml of ice-cooled acetone with stirring. After cooling the mixture overnight, a solid product formed which was collected by filtration, again dissolved in 30 ml of water, and dropwise added to 150 ml of acetone to precipitate a solid product. The solid product thus formed was collected by filtration, dissolved in 30 ml of water, and added dropwise to 200 ml of ice-cooled ethanol with stirring. After cooling overnight, the solid product which formed was collected and dried thereby yielding a crude product containing 7.0 g (70.0% in purity) of sodium 7 β-[D-(−)-α-(4-carboxyimidazole-5-carboxamido)-phenylacetamido]-3-(4-β-sulfoethylpyridinium)methyl-3-cephem-4-carboxylate having the formula:

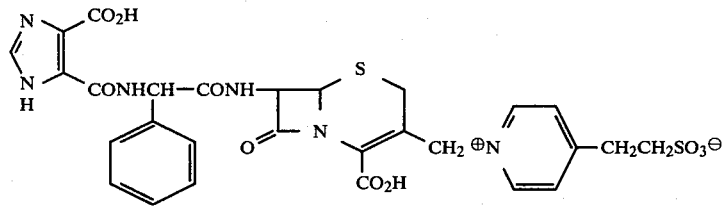

Thereafter, 13.7 g of the crude product was dissolved in 400 ml of 30° C. water, and 6 N hydrochloric acid was added thereto to adjust the pH to 2. After continuing the stirring for 30 minutes, a precipitate formed which was removed by centrifugation, and the mother liquor was concentrated at 30° C. under reduced pressure to a quantity of 80 g. To this concentrate was added 400 ml of ethanol with stirring and, after being cooled to 10° C., the solution was allowed to stand for one hour. A precipitate formed which was collected by filtration under reduced pressure, and dried in vacuo at 40° C. to obtain 10.1 g of powder containing 8.6 g of the end product.

Further, water was added to 10.1 g of this powder to make a 100 ml solution, and 25 ml of a nonionic absorbing resin, "Amberlite XAD-7", was added thereto. After stirring for 30 minutes at room temperature, the resin was removed by filtration, and the resin was washed with 50 ml of water. The mother liquor and the washings were combined and concentrated at 30° C. to yield 70 g of a concentrate. A 350 ml amount of ethanol was added to this concentrate with stirring, and the resulting solution was cooled to 10° C. and allowed to stand for one hour. A precipitate formed which was separated by filtration under reduced pressure and dried in vacuo to yield 7.3 g of the desired end product (yield: 73%). Reverse phase thin layer chromatography (TLC) of 20 μg of the product showed a single spot. On the other hand, reverse phase TLC of 20 μg of the crude product obtained before the purification procedure yielded four spots.

EXAMPLE 2

A 13.7 g amount of a crude product (containing 9.6 g of the end product) prepared according to the procedures described in Example 1 was dissolved in 500 ml of water at 10 C. and the pH of the solution was adjusted to 2 by the addition thereto of 6 N sulfuric acid. After continued stirring for 30 minutes, a precipitate formed which was removed by centrifugation, and the mother liquor was concentrated at 30° C. under reduced pressure to a quantity of 80 g. To this concentrate was added, with stirring, 400 ml of ethanol. After being cooled to 10° C., the solution was allowed to stand for one hour, and the precipitate thus formed was separated by filtration under reduced pressure and dried in vacuo at 40° C. to obtain 9.6 g of a powder containing 7.7 g of the end product.

Thereafter, water was added to 9.6 of this powder in an amount sufficient to form a 76 ml solution. This solution was passed through a resin tower containing 100 ml of a nonionic absorbing resin, "Amberlite XAD-7", and fractions containing the end product were collected. The fraction was concentrated at 30° C. to yield 60 g of a concentrate. A 300 ml amount of ethanol was added to the concentrate with stirring. After being cooled to 10° C., the solution was allowed to stand for one hour, and a precipitate formed which was collected by filtration under reduced pressure and dried in vacuo at 40° C. to obtain 6.9 g of the desired end product (yield: 72%). Reverse phase TLC of 20 μg of this substance gave a single spot.

EXAMPLE 3

A 13.7 g amount of a crude product (containing 9.6 g of the desired end product) prepared according to the procedure described in Example 1 was dissolved in 400 ml of 30° C. water, and the pH of the solution was adjusted to 2.5 by adding 6 N hydrochloric acid thereto. After continuing stirring for 30 minutes, a precipitate formed which was removed by filtration, and the mother liquor was concentrated to a quantity of 80 g at 30° C. under reduced pressure. A 400 ml amount of ethanol was added, with stirring, to this concentrate. After being cooled to 10° C., the solution was allowed to stand for 1 hour, and a precipitate formed which was separated by filtration under reduced pressure, and dried in vacuo at 40° C. thereby obtaining 10.1 g of powder containing 8.6 g of the desired end product.

Additionally, water was added to 9.6 g of this powder in an amount sufficient to form a 80 ml solution, and the resulting solution was passed through a resin tower containing 100 ml of a nonionic absorbing resin, "Diaion HP-3MG" (manufactured by Mitsubishi Chemical Industries, Ltd.), and fractions containing the end product were collected. The fractions were then concentrated at 30° C. thereby yielding a 70 g concentrate. A 350 ml amount of ethanol was added to this concentrate with stirring. After being cooled to 10° C., the solution was allowed to stand for one hour, and a precipitate formed which was separated by filtration under reduced pressure, and dried at 40° C. to yield 7.7 g of the end product (yield: 80%). Reverse phase TLC of 20 μg of this substance yielded a single spot.

Having now fully described this invention, it will be apparent to one of ordinary skill in the art that many changes and modifications can be made thereto without departing from the spirit or scope of the invention as set forth herein.

What is claimed as new and is desired to be secured by Letters Patent is:

1. A method for purifying a cephalosporin compound of the formula:

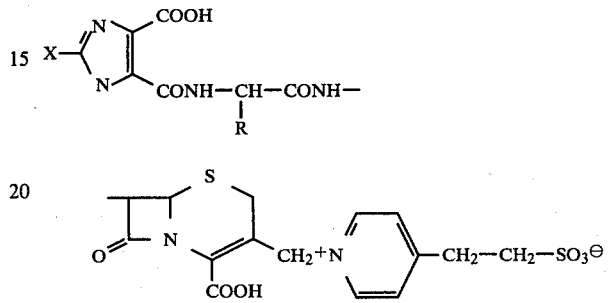

wherein X is hydrogen, halogen, hydroxy, alkyloxy, phenylalkyloxy, phenyloxy, mercapto, alkylthio, phenylalkylthio, phenylthio, alkylsulfonyl, phenylalkylsulfonyl, phenylsulfinyl, alkylsulfinyl, phenylalkylsulfinyl, phenylsulfinyl, amino, mono- or di-alkylamino, mono- or di-phenylalkylamino, mono- or di-phenylamino, alkanoylamino, a sulfonic acid group, nitro, alkyl, phenylalkyl, or phenyl; and R is hydrogen, alkyl, phenylalkyl, or phenyl, with all of the alkyl, phenylalkyl, and phenyl groups in radicals X and R optionally being substituted with at least one substituent, comprising:

(a) adjusting the pH of an aqueous solution containing said cephalosporin compound to be purified to within the range of 1.0 to 3.5;

(b) removing the compound which precipitates from said solution, whereby a mother liquor is left behind;

(c) concentrating the mother liquor, adding the mother liquor after said concentrating to an organic solvent, isolating the precipitated compound and agitating the obtained compound in an aqueous solution in the presence of an absorbing resin which is a hydrophilic, high molecular weight material having a fine network structure; and (d) isolating the purified compound.

2. The method of claim 1, wherein said pH is adjusted over a range of 1.5 to 2.5.

3. The method of claim 1, wherein the pH of said aqueous solution is adjusted by the addition of an inorganic acid or organic acid to said solution.

4. The method of claim 3, wherein said inorganic acid is hydrochloric acid, sulfuric acid or nitric acid and said organic acid is oxalic acid, formic acid or acetic acid.

5. The method of claim 1, wherein the temperature of said aqueous solution containing said cephalosporin compound is maintained at a temperature of 10° to 35° C. when the pH of said solution is adjusted.

6. The method of claim 1, wherein said compound is precipitated by adding a 3- to 7-fold amount of an organic solvent to said solution containing said cephalosporin compound at a temperature of 5° to 20° C.

7. The method of claim 1, wherein in step (c) water is added to the previously precipitated compound in an amount to formulate a solution containing 5–20% of said cephalosporin compound.

8. The method of claim 1, wherein from 0.1 to a tenfold amount of a hydrophilic, high molecular weight resin is mixed with said aqueous solution.

9. The method of claim 1, wherein, after said resin is separated from said solution, the resin free solution is concentrated to a level of 10–15% at a temperature of 20° to 30° C., and subsequently a 3- to 7-fold volume amount of an organic solvent is mixed with said resin free concentrated solution at 5° to 20° C. to precipitate the desired purified cephalosporin product.

* * * * *